United States Patent [19]
Matsumoto

[11] Patent Number: 5,019,434
[45] Date of Patent: May 28, 1991

[54] MOLDED SLOW-RELEASE AIR FRESHENER

[75] Inventor: Yuichi Matsumoto, Abiko, Japan

[73] Assignee: Soda Aromatic Co., Ltd., Tokyo, Japan

[21] Appl. No.: 427,977

[22] Filed: Oct. 26, 1989

Related U.S. Application Data

[63] Continuation-in-part of Ser. No. 69,293, Jul. 2, 1987, abandoned.

[30] Foreign Application Priority Data

Jul. 8, 1986 [JP] Japan .................................. 61-158779

[51] Int. Cl.$^5$ .............................................. A61L 9/04
[52] U.S. Cl. ...................... 428/35.7; 239/54; 239/55; 264/126; 428/36.92; 428/143; 428/308.4; 428/323; 428/905
[58] Field of Search .................. 428/35.7, 36.92, 143, 428/323, 308.4, 905, 35, 522; 239/6, 54, 55, 57; 264/126, 128

[56] References Cited

U.S. PATENT DOCUMENTS

| | | | |
|---|---|---|---|
| 4,438,010 | 3/1984 | Lindauer et al. | 264/126 |
| 4,445,641 | 5/1984 | Baker et al. | 239/6 |
| 4,460,530 | 7/1984 | Hanson et al. | 264/126 |
| 4,515,909 | 5/1985 | Sawano et al. | 428/905 |

Primary Examiner—James J. Seidleck
Attorney, Agent, or Firm—Scully, Scott, Murphy & Presser

[57] ABSTRACT

A molded slow-release air freshener prepared by having a liquid perfume composition absorbed into a porous molded product which has been obtained by partially melt-bonding the particles of an ethylenevinyl acetate copolymer powder with each other to obtain said porous molded product having continuous gas-permeable pores and a bulk density in the range of 0.4 to 0.8 g/cm$^3$, said molded slow-release air freshener having an increased apparent volume of at least 1.2 times as large as its apparent volume before the absorption of said liquid perfume composition.

41 Claims, 4 Drawing Sheets

MOLDED SLOW-RELEASE AIR FRESHENER

This application is a continuation-in-part of application Ser. No. 069,293, filed July 2, 1987, now abandoned.

BACKGROUND OF THE INVENTION

The present invention relates to a novel molded air freshener.

Various proposals have heretofore been offered about air fresheners using various kinds of thermoplastic resins and perfumes supported thereon.

Ethylene-vinyl acetate copolymer resin (hereinafter referred to simply as "EVA") absorbs perfumes most easily among all thermoplastic resins and it permits the absorbed perfumed to exhibit volatilizing properties which are extremely superior. And air fresheners using EVA of such superior characteristics as perfume carriers halve come to appear in this industry as "plastic-based" air fresheners. They are morphologically classified broadly into two types —(a) a pellet type in which perfumes are absorbed in molding pellets of EVA resin and (b) a molded product type in which perfume-absorbed EVA pellets, as molding material, are melt-molded directly according to a known molding method such as, for example, injection molding or extrusion.

The pellet type (a) is advantageous in that there is no fear of degradation of perfume because a pellet type air freshener is prepared by contacting a perfume with EVA pellets for several hours at a room temperature or thereabouts. However, since the pellets are apt to fall from their container, it is inevitably necessary for the container to be a closed type having vent slits smaller in diameter than the pellets. For this reason and because of pellets, the decrease of volume caused by volatilization of the perfume is small and so it is difficult to visually perceive an end point indicating the end of the volatilization.

The molded product type (b) is advantageous in that because of a melt-molded product of a perfume-containing EVA, the decrease of volume caused by volatilization of the perfume is larger than that in pellets and so it is easy to perceive the aforesaid end point easily. But it is disadvantageous in that the heat deterioration of perfume is unavoidable because the molding temperature reaches 100° C. or so even at the lowest.

To make up for such drawback, first EVA alone may be subjected to molding and then the resultant molded product immersed in a perfume at room temperature, allowing the perfume to be adsorbed in the molded product. In this method, however, an extremely long time is required for the absorption, and due to the absorption after molding, there occur distortional deformations and roughening of the surface, often resulting in marked impairment of the external appearance. Therefore, the products obtained by such method are difficult to use practically and in fact no products that are presumably obtained by such method are on the market.

SUMMARY OF THE INVENTION

It is an object of the present invention to overcome the above-mentioned drawbacks of the prior art.

It is a further object of the present invention to provide a novel, molded, slow-release air freshener formed from EVA, capable of absorbing as carrier a large amount of a perfume at a room temperature in an extremely short time, the thus perfume-absorbed air freshener being highly volatile, exhibiting a large reduction in volume with volatilization of the perfume and hence permitting easy visual perception of an end point of the volatilization.

The present invention resides in molded slow-release air fresheners prepared by melt-bonding the particles of EVA powder with each other to obtain a porous molded product having continuous gas-permeable pores and a bulk density in the range of 0.4 to 0.8, g/cm$^3$ and then allowing the porous molded product to absorb a liquid perfume composition, and thereby having an apparent volume at least 1.2 times as large as the value before the absorption.

The present invention further provides a process for producing the molded, slow-release air freshener. The practice of the present inventive process involves providing an ethylene vinyl acetate copolymer powder in the form of a sheet. The powder may be placed on a support, such as a plate or belt. The powder is heated, as for example, by the support itself, in order that the particles of ethylene vinyl acetate copolymer will partially melt bond with each other and thus form a porous sheet-like product having continuous gas-permeable pores and bulk density in the range of 0.4 to 0.8 g/cm$^3$. The heating may occur without the application of pressure.

This porous, sheet-like product may be further cut into a desired shape, if necessary, such as, for example, a plate or circle-like shape, or an equilateral polygon-like shape. In a preferred embodiment, the porous sheet-like product is cut into a multiplicity of smaller porous sheet-like products of desired shape. A porous sheet-like product thus obtained is impregnated with a liquid perform composition. The impregnation can occur before or after the porous product is set into a holder; the holder being in close fitting relationship with the porous product and disposed about at least a portion of an edge of the porous product. The inside of the holder may also have a design that tapers off at least at those portions disposed about the porous product. This is, the walls of their interior sides, angle inwardly. This would facilitate the bending or shifting toward the vertical direction, the later expansion of the porous product. A container may be used as a holder, for example a container which engages the perimeter of the porous product. The container may have a surface area about the same as the surface area of the porous sheet-like product, and may have a circular surface shape.

In an optimal embodiment, the holder may engage at least a portion of the perimeter of the porous sheet-like product to retain it in fixed relationship to the holder. In another embodiment, the holder is disposed about the porous-like sheet in a fashion so that upon subsequent impregnation with the perform composition the porous product expands to engage the sides of the holder thereby retaining the porous product within the confines of, for example, the side(s), the wall(s), or the protruding-edge(s) of the holder.

The liquid perform composition may be comprised of a perfume or a perfume and a solvent. The weight percentage of the liquid perform composition in the finished product (copolymer plus perfume composition) is not lower than the weight percentage of the vinyl acetate in the ethylene vinyl acetate copolymer. The liquid perfume composition is absorbed into the porous product; either before or after placement of the porous product into the holder or container. The absorption results in the expansion of the porous product. The expansion may be in three-dimensions and, depending upon the shape of the cut porous sheet-like product and that of the holder or container, a transfiguration in appearance occurs.

For example, a plate-like assembly of porous product and container or holder results in a hemispheric shape; the hemisphere may have a hollow space between the porous molded product and the corresponding container or holder. The hollow, hemispheric shape occurs at least around the center of the absorbed porous molded product. Prior to this absorption, the porous product may be increased to a size of at least 1.06 times greater than its size before the absorption of the liquid perfume composition. This would effect, for example, the appearance of the expanded or transfigured product.

DETAILED DESCRIPTION OF THE INVENTION

Before explaining the construction of the present invention, the following description is now provided about the peripheral techniques which the present inventor has studied. It is a self-evident truth that when liquid is to be absorbed into a substance having absorbability, the larger the absorbing surface area, the higher the rate of absorption. This principle also applied to the case where a perfume is to be absorbed into EVA; that is, pellets absorb the perfume more rapidly than a molded product having a certain volume, and powder, more rapidly than pellets. In the case where 30 wt. % of a perfume is added to EVA powder having an average particle diameter of 0.5 mm (32 mesh) or so, the absorption is completed within only several ten seconds if the content of vinyl acetate (hereinafter referred to simply as "VA") is 32%, and even when the VA content is 20%, reflected in a little lower absorbability, the absorption is completed without requiring several minutes and the perfume permeates the powder rapidly, which reverts to the original dry powdered state although the fluidity is somewhat deteriorated. However, this perfume-absorbed EVA powder is extremely thin and so, aside from the case where it is spread over a large area, its volatilizability is markedly deteriorated if it is charged into a container having a certain depth like a conventional air freshener, and in this case, upon termination of the volatilization from the surface layer over a period of initial several days, the volatilization scarcely proceeds any further with the result that only about 20% of the perfume contained is utilized. This is why a perfume-containing EVA powder is not utilized as a perfumer or air freshener notwithstanding its advantage that it can absorb a large amount of perfume rapidly at a room temperature. This is because the perfume-absorbed powder particles are isolated from one another so the movement of perfume between the particles (from the particles larger in the perfume content to the particles smaller in the same content) is not performed at all and also because the gap between adjacent particles is small so the movement of the perfume vapor from the lower to the upper layer is scarcely performed. The present invention, which is effective remarkably, has been completed through such studies.

The molded product of EVA serving as carrier in the present invention is essentially a porous molded product having continuous gas-permeable pores and a bulk density in the range of 0.4 to 0.8, obtained by partially melt-bonding the particles of EVA powder with each other. Such partially melt-bonded, molded product of EVA powder absorbs, for example, the same weight of a perfume as the weight of the molded product in an instant at a room temperature, and at the same time the permeation of the perfume into the powder also proceeds rapidly. And within only several minutes the thus perfume-absorbed molded product becomes a completely dried spongy molded product rich in elasticity and having continuous gas-permeable pores. The expansion of the partially melt-bonded, molded product at this time is extremely large, reaching, for example, 1.9 times in terms of volume, 1.6 times in terms of surface area, as large as its original size. And the volatilizing property of the perfume from this spongy perfume-absorbed molded product is almost the same as that from a perfume-containing melt-molded product having the same weight, same perfume content and same volatilization area, obtained according to an injection molding method. In the present invention, moreover, if the partially melt-bonded, molded product of EVA serving to absorb a perform is formed in the shape of a thin disc and then placed in a shallow can-like container which engages the container closely, followed by fixing of the outer edge and addition of a perform, the thin disc will swell in the direction of its upper surface because its expansion in a centrifugal direction is prevented by the container wall. As a result, there can be obtained easily a perform-absorbed product which is hollow and hemispheric like a hollow ball cut in half.

The partially melt-bonded, molded product of EVA powder serving as a perform absorbing carrier in the present invention is obtained easily by charging EVA powder into a mold of a desired shape, followed by heating for a predetermined time in an oven held at a predetermined temperature.

The mold for melt bonding and molding may take any desired shape, but preferably it is as thin as possible in order to shorten the time required for melt molding and enhance the volatilization efficiency of the perfume absorbed into the partially melt-bonded, molded product. Further, when the distortion induced at the time of expansion of the molded product in a perfume-absorbed state is considered, a circular shape is desirable. Provided, however, that the application of pressure to the fed EVA powder during heating must be avoided because it would impede the formation of continuous gas-permeable pores which is the most important feature of the partially malt-bonded, molded product. Therefore, it is most desirable that the upper portion of the mold be open thereby allowing the powder to be melt-bonded under its own weight alone.

The EVA powder used for forming the partially melt-bonded, molded product may be any of commercially available ones ranging in VA content from 40% to 6%. The amount of perfume absorbed is approximately proportional to the VA content, and the degree of expansion of the partially melt-bonded, molded product caused by its absorption of perfume is proportional to the amount of perfume absorbed. In addition, the heat resistance, etc. of the perfume-absorbed, partially melt-bonded, molded product must also be taken into consideration. In view of these points, it is preferable that the VA content be in the range of between 33% and 20%, for the ordinary purpose of an air freshener which requires a perfume content of about 20-40 wt. %. (Provided that in the case where resistance to heat of 90° C. or so is required, for example in the case of an air freshener for an automobile cabin, it is necessary to use EVA powder whose VA content is 10% or thereabouts.)

The smaller the particle size (average particle diameter) of the EVA powder, the larger the number of melt-bounded points between the particles and hence the higher the physical strength (against external forces such as warp and bend) of the perfume-absorbed spongy molded product. Therefore, it is desirable that the particle size (average particle diameter) be as small as possible. In the case of a flat disc-like molded product, a particle size of 30 mesh (0.5 mm dia.) or so fully permits attainment of the desired purpose. But in the case of molding into a hemispheric shape utilizing the expanded force at the time of perfume absorption as previously noted, it is desirable to use EVA powder not larger than 60 mesh (0.25 mm) in order to resist the tension.

An optimum melt-bonding temperature as a reference temperature corresponds to a melting point (hereinafter referred to simply as "MP") temperature inherent in EVA powder. At this temperature it is possible to attain uniformity without giving rise to difference in the degree of melt bonding between the surface and a deep portion even when the desired partially melt-bonded, molded product is thick, requiring a considerable time. However, it is necessary that the optimum melt bonding temperature be somewhat shifted in a plus or minus direction depending on the magnitude of the melt flow index [M.I. ASTM-D1238-73 (hereinafter referred to simply as "MI")]. This is because of the tendency that in the case of EVA powder having a large MI there occurs flow deformation of the powder particles even under heating at the MP temperature, so that melt bonding proceeds to excess beyond the melt bonding at contact points, while in the case of EVA powder having a small MI the melt bonding at contact points become somewhat incomplete. The optimum melt bonding temperature taking such MI into account is approximately in the range of MP−7° C. to MP+4° C.

For example, in the case of "Ultrathene UE-750" powder which is EVA manufactured by Toyo Soda Manufacturing Co., Ltd., having VA content 32%, MI 30 and MP 70° C., which is used most frequently as a perfume absorbing carrier, its optimum melt bonding temperature corresponds to its MP, i.e., 70° C. But in EVA powders extremely large in MI such as, for example, "Ultrathene UE-720" having VA content 28%, MI 150 and MP 74° C. and "Ultrathene UE-681" having VA content 20%, MI 350 and MP 85° C., their optimum melt bonding temperatures are 69° C. (MP−5° C.) and 78° C. (MP−7° C.), respectively. On the other hand, in the cases of "Ultrathene UE-634" having VA content 26%, MI 4 and MP 79° C. and "Ultrathene UE-540" having VA content 10%, MI 3 and MP 97° C., their optimum melt bonding temperatures are 82° C. (MP+3° C.) and 101° C. (MP +4° C.), respectively. The heating time differs depending on the mold shape and the thickness of the EVA powder layer, but a standard heating time is approximately 25 to 30 minutes in the foregoing temperature range provided the thickness is 10 mm or thereabouts. If the thickness is about 3 to 5 mm, it is possible to shorten the heating time, using a temperature higher than the above optimum temperature range, because in such a degree of thickness there is no large deviation in heat reaching time between the surface layer and the central portion. For example, in the case where "Ultrathene UE-634" having VA content 26%, MI 4 and MP 79° C. is charged into a 5 mm deep mold up to the brim of the mold and subjected to melt bonding and molding, standard conditions involve a temperature of 82° C. (MP+3° C.) and a period of 30 minutes, but even under the conditions of 99° C. (MP+20° C.), 11 minutes, it is possible to obtain about the same degree of bonding. An appropriate melt bonding degree can roughly be determined from the appearance and color of the resulting partially melt-bonded, molded product. The degree of melt bonding can be judged in such a manner that the melt-bonded state is unsatisfactory when the product maintains the whiteness of the original powder, while it is excessive when the transparency is to a considerable extent. A more accurate way of judgment uses "bulk density" (weight of partially melt-bonded molded product/volume of the same product). The following table shows examples of melt bonding temperatures and bulk densities at optimum melt bonding degrees of partially melt-bonded, molded products using various EVA powders.

|  | MI | VA (%) | MP (°C.) | Melt Bonding Temperature (°C.) | Bulk Density (g/cm$^3$) |
| --- | --- | --- | --- | --- | --- |
| Ultrathene UE-750 | 30 | 32 | 70 | 70 (MP ± 0) | 0.622 |
| Ultrathene UE-720 | 150 | 28 | 74 | 69 (MP − 5) | 0.597 |
| Ultrathene UE-710 | 18 | 28 | 75 | 76 (MP + 1) | 0.629 |
| Ultrathene UE-634 | 4 | 26 | 79 | 82 (MP ± 3) | 0.567 |
| Ultrathene UE-681 | 350 | 20 | 85 | 78 (MP − 7) | 0.578 |
| Ultrathene UE-633 | 20 | 20 | 86 | 86 (MP) | 0.606 |
| Ultrathene UE-540 | 3 | 10 | 97 | 10.1 (MP + 4) | 0.563 |

The larger the numerical value of the "bulk density", the higher becomes the degree of melt bonding, the lower the perfume absorbing speed, the smaller the absorption quantity and the smaller the expansion coefficient, but the physical strength of the resulting perfume-contained molded product becomes higher. Conversely, the smaller the numerical value, the lower becomes the degree of melt bonding and the larger become the perfume absorption quantity, absorption speed and expansion coefficient, but the physical strength of the resulting perfume-absorbed molded product becomes lower. Therefore, when a large strength enough to resist tension is required as in the case where the outer edge of a disc-like, partially melt-bonded, molded product is fixed, then a perfume is allowed to be absorbed therein and the resulting expansion causes the molded product to change in shape into a hollow hemisphere, as previously noted, the requirement can be satisfied by effecting the melt bonding and molding so as to enlarge the above numerical value, that is, somewhat to excess. On the other hand, when a larger expansion and an increase in the amount of perfume absorbed are required rather than strength, this requirement can be met by performing the melt bonding and molding so as to make the above numerical value smaller, that is, somewhat deficiently. However, the preferred numerical range of bulk density should be between 0.4 and 0.8 g/cm$^3$. Outside this range (below 0.4 g/cm$^3$), the molded product will revert to its original powdery form upon absorption of perfume, or outside the said range (above 0.8 g/cm$^3$), the molded product will be nearly a melt-molded product requiring several ten hours for the absorption of perfume.

As to the perfume to be absorbed into the partially melt-bonded, molded product of EVA powder, there are some restrictions as in the case of a melt-molded product or pellets of EVA. Since the EVA resin is difficult to absorb a component having large polarity, it is desirable to avoid using a mixed perfume which contains a large excess of such ingredient as an alcohol, or a mixed perfume which contains a polyhydric alcohol solvent, e.g. a glycol, as a diluent or an extender.

If the mixed perfume used has been prepared in consideration of the above points, the partially melt-bonded, molded product of EVA powder absorbs it in an instant at a room temperature in an amount much larger than that in the use of a melt-molded product or pellets of EVA, allowing the perfume to permeate completely into a deep portion of the powder within a short time expressed in the unit of "minute", so that there remains no perfume in the continuous gas-permeable pores, thus affording a porous, spongy, perfume-absorbed product comprising continuous pores in a completely dried state free from wetting even when touched with a finger. In general, the perfume absorbability of a melt-molded product or pellets of EVA is proportional to the VA content thereof and the maximum absorptivity is almost equal to the numerical value of the percent VA content thereof. For a larger absorption it may be necessary to prolong the absorption time and to heat for the absorption, which are unprofitable. Besides, even after such absorption, there often arise inconveniences; for example, the surface of the melt-molded product or pellets of EVA become rough, or excess perfume oozes out when the temperature is low. However, in the case of a partially melt-bonded, molded product of EVA powder used as a perfume absorber in the present invention and having a standard degree of melt bonding [corresponding to one obtained by heating (melt bonding temperature: 70° C.) the foregoing "Ultrathene UE-750" of VA content 32% and MP 70° C. at 71° C. for 30 minutes], it exhibits a perfume absorptivity of a numerical value of the percent VA content, e.g. 51% absorptivity for 32% VA content, 41.6% absorptivity for 26% VA content, and 32% absorptivity for 20% VA content. Where the melt bonding is performed to a somewhat weaker extent than the standard degree of melt bonding by either lowering the heating temperature or shortening the heating time, it is possible to effect the absorption to a greater extent than the above magnification. Conversely, if the melt bonding is done to a somewhat stronger extent, it is possible to enhance the physical strength of the perfume absorber although the absorptivity becomes a little lower than the above standard value.

Therefore, if there is fabricated a container as a final commodity in conformity with an expansive volume or surface area and a partially melt-bonded, molded product is placed therein followed by adsorption of a perfume, there is obtained a perfume-absorbed molded product expanded up to the brim of the container, while if a disc-like, partially melt-bonded, molded product is placed in a circular container having a diameter for close fitting round the disc-like molded product followed by absorption of a perfume, there is obtained a hemispheric molded product like a hollow ball cut in half easily upon expansion.

In forming such hollow hemispheric product utilizing the expansion caused by the absorption of perfume, it is desirable to increase the number of melt-bonded points by using a fine EVA powder not larger than 60 mesh as previously noted so as to have resistant to the tension induced at the time of expansion. Further, in order to enhance the melt bonding strength, it is desirable to select EVA powder of a small MI value, e.g. "Ultrathene UE-634" (MI 4).

The larger the thickness of the partially melt-bonded, molded product, the larger become the apparent volume and strength of the resulting hemispheric molded product. However, if the thickness is made large beyond a certain limit, the shape retaining force of the partially melt-bonded, molded product itself whose outer edge is restrained by the wall of a container or the like becomes larger than the upwardly expanding force, so that the upward expansion becomes extremely slight or almost zero and hence it is no longer possible to obtain a hemispheric molded product.

Partially melt-bonded, molded products were prepared using a fine powder of "Ultrathene UE-634" not larger than 60 mesh and using nine kinds of melt bonding molds 75 mm in diameter and respectively having depths of 1.5 mm (thickness/diameter=0.02), 2.5 mm, 5 mm, 7.5 mm, 10 mm, 12.5 mm, 15 mm, 17.5 mm (thickness/diameter=0.23) and 20 mm (thickness/diameter=0.27). Then, they were each fitted in a circular can 75 mm in diameter and 20 mm in depth, and a perfume was absorbed into each of them in an amount of 41.6% (% VA content 26×1.6=41.6%) in terms of a perfume content of the resulting perfume-absorbed product. In this experiment, those of 1.5 mm up to 17.5 mm became hemispheric upon expansion although there was a difference in hardness which was attributable to the difference in thickness and there also was a difference in apparent volume. But the one 20 mm in thickness merely protruded about 2 mm at its central portion and remained high in density not fully expanded. Thus, the range which permits hemispheric molding on expansion is approximately between 0.02 and 0.25 in terms of numerical values of thickness/diameter. The perfume absorbability of the partially melt-bonded, molded product of EVA powder is extremely large as mentioned above, so where the amount of perfume to be absorbed is too small, for example when only 10 to 15 wt. % of a perfume is added to a partially melt-bonded, molded product of EVA having a VA content of 32%, the absorption of the perfume will be localized only at a portion of the melt-bonded molded product, leaving an unabsorbed portion. This is not only inconvenience in appearance but also causes a strong distortion at the boundary surface between the expanded absorbed portion and the unabsorbed portion, leading to the occurrence of crack or deformation. Therefore, the amount of perfume to be added must be not less than a minimum amount sufficient to permit absorption and permeation of the perfume over the entire surface of the partially melt-bonded molded product. The said minimum amount required is approximately 1.2 times the numerical value of the percent VA content. However, when weak fragrance is required as in the case of an indoor or vehicular air freshener, the amount of perfume used must inevitably be kept low and hence the resulting perfume-absorbed molded product is compelled to be small-sized accordingly. But from the standpoint of appearance, a certain lower limit of volume is in some case preset for the perfume-absorbed molded product. In this case, the amount of perfume used sometimes becomes smaller than the minimum amount required.

In such case, an odorless or slightly-odored hydrocarbon or ester solvent may be added to the perfume to dilute and increase the amount of the perfume up to the minimum amount required followed by absorption. As hydrocarbon solvents are preferred odorless n-paraffins and isoparaffins, while as ester solvents are preferred those used as plasticizers for plastics and those as extenders for perfumes such as, for example, diethyl phthalate, dimethyl phthalate, dioctyl phthalate, diisotutyl adipate, and dioctyl adipate. Polyhydric alcohol solvents having large polarity, e.g. dipropylene glycol, polyethylene glycol and hexylene glycol, must not be used even though they are odorless solvents because they are not absorbed into the partially melt-bonded, molded product as previously noted.

A perfume or a mixture thereof with an odorless hydrocarbon or ester solvent can be absorbed into the partially melt-bonded, molded product of EVA powder by a simple method of dripwise adding or sprinkling the perfume or mixture onto the surface of the molded product. This is because the dripwise added or sprinkled perfume or mixture thereof with the odorless solvent is rapidly permeated and absorbed uniformly over the entire surface of the partially melt-bonded, molded product of EVA powder and also into the interior thereof. The perfume-volatilizable molded product thus obtained can be colored easily by either (1) dissolving an oil-soluble dye of a desired color beforehand into the perfume or perfume-odorless solvent mixture used, or (2) mixing in advance a pigment of a desired color intimately into the EVA powder which is used for melt bonding.

The present invention has the following effects.

(1) An extremely long time is required for contacting a perfume in an amount as large as 30 wt. % or more with a melt-molded product of EVA and thereby impregnating and absorbing it into the molded product at an ordinary temperature. Even in the case of pellets as moldings of a minimum unit, several hours are required, and in the case of a larger molded product, for example in the case of a melt-molded product of EVA such as one to be described in Example 5 as stated below, a long time of 12 to 24 hours is required. On the other hand, the partially melt-bonded, molded product of EVA powder according to the present invention absorbs a perfume in an amount as large as 40 to 50 wt. % in only several ten seconds to several minutes at the latest.

(2) Although the absorption is completed in such short time, the perfume-absorbed, partially melt-bonded, molded product of EVA powder is a completely dried condition, that is, there is neither exudation of the perfume nor wetting, so even when one touches it with a finger, the finger will not be stained at all.

(3) As previously noted, the partially melt-bonded, molded product of EVA powder exhibits a very large expansion in volume upon absorption of a perfume, so its contraction caused by volatilization of the absorbed perfume is also very marked. Consequently, the termination (so-called end point) of the perfume volatilization can be judged easily by such change in appearance.

(4) If a plate-like, partially melt-bonded, molded product of EVA powder having an appropriate thickness is fitted in a container which is in close fitting relation thereto followed by pouring of a perfume or a liquid mixture thereof with a hydrocarbon or ester solvent, allowing the perfume to be absorbed into the molded product, then it is possible to easily obtain a product having cubic effect under expansive action; for example, in the case of a disc-like, partially melt-bonded, molded product, there can be easily obtained a hemispheric, perfume-absorbed, molded product like a hollow ball cut in half.

The following examples are given to illustrate the present invention in more detail and more concretely, but it is to be understood that the invention is not limited thereto.

EXAMPLE 1

7 g of powder wholly passing through 32 mesh (average particle diameter: 0.5 mm) of EVA, trade name "Ultrathene UE-750" (MI 30, VA content 32 wt. %, MP 70° C.), a product of Toyo Soda Manufacturing Co., Ltd., was charged into a metallic, can cap-like melt-bonding mold having a diameter of 56 mm and a depth of 7 mm, up to the brim of the mold, under application of slight pressure, (bulk density at this time: 0.406 g/cm$^3$). Then, the mold was placed and heated in a constant temperature bath held at 71° C., and when the temperature of a temperature measuring melt-bonding mold with a thermocouple embedded therein and charged with the above EVA powder, also placed in the same constant temperature bath, indicated 70° C. (MP of UE-750)(after exactly 30 minutes), the can cap-like mold was taken out and cooled to room temperature. Then, the contents of the mold was removed from the mold to obtain a somewhat elastic, porous, melt-bonded, molded product having the appearance of a powder aggregate and having continuous gas-permeable pores, 56 mm in diameter and 4.5 mm in thickness. Its bulk density was 0.632 g/cm$^3$. This melt-bonded, molded product was chipped with a sharp edged tool and observed through a microscope of low magnification. As a result, the molded product was found to be of a porous structure having continuous gas-permeable pores in which the powder particles were melt-bonded together only at their contact points while retaining the individual shapes though somewhat deformed thermally.

Further, the melt-bonded, molded product thus obtained was tested for gas permeability using the smoke of tobacco. As a result, the smoke passed through the molded product easily even with little breathing pressure applied, and thus the gas permeability of the molded product was demonstrated.

This disc-like, melt-bonded, molded product was placed in a tin can having a diameter of 70 mm and a depth of 10 mm and then 7 g (corresponding to 50% perfume content) of a fragrant olive type mixed perfume pre-colored into orange color with an oil-soluble dye was poured onto the central part of the surface of the melt-bonded, molded product. As a result, in an instant of 10 to 15 seconds the perfume was diffused and permeated over the whole surface of the melt-bonded, molded product. Then, while expanding the molded product gradually, the perfume was absorbed into each of the powder particles as constituents of the molded product, and in only two minutes there was obtained a strong, spongy, elastic product in a dried condition in which there occurred neither wetting nor stain with the perfume even under the application of a finger tip pressure, that is, in a state with no perfume remaining in the continuous gas-permeable pores of the melt-bonded, molded product. The expansion ratio was 1.6 times the original size in terms of surface area.

Figure 1:
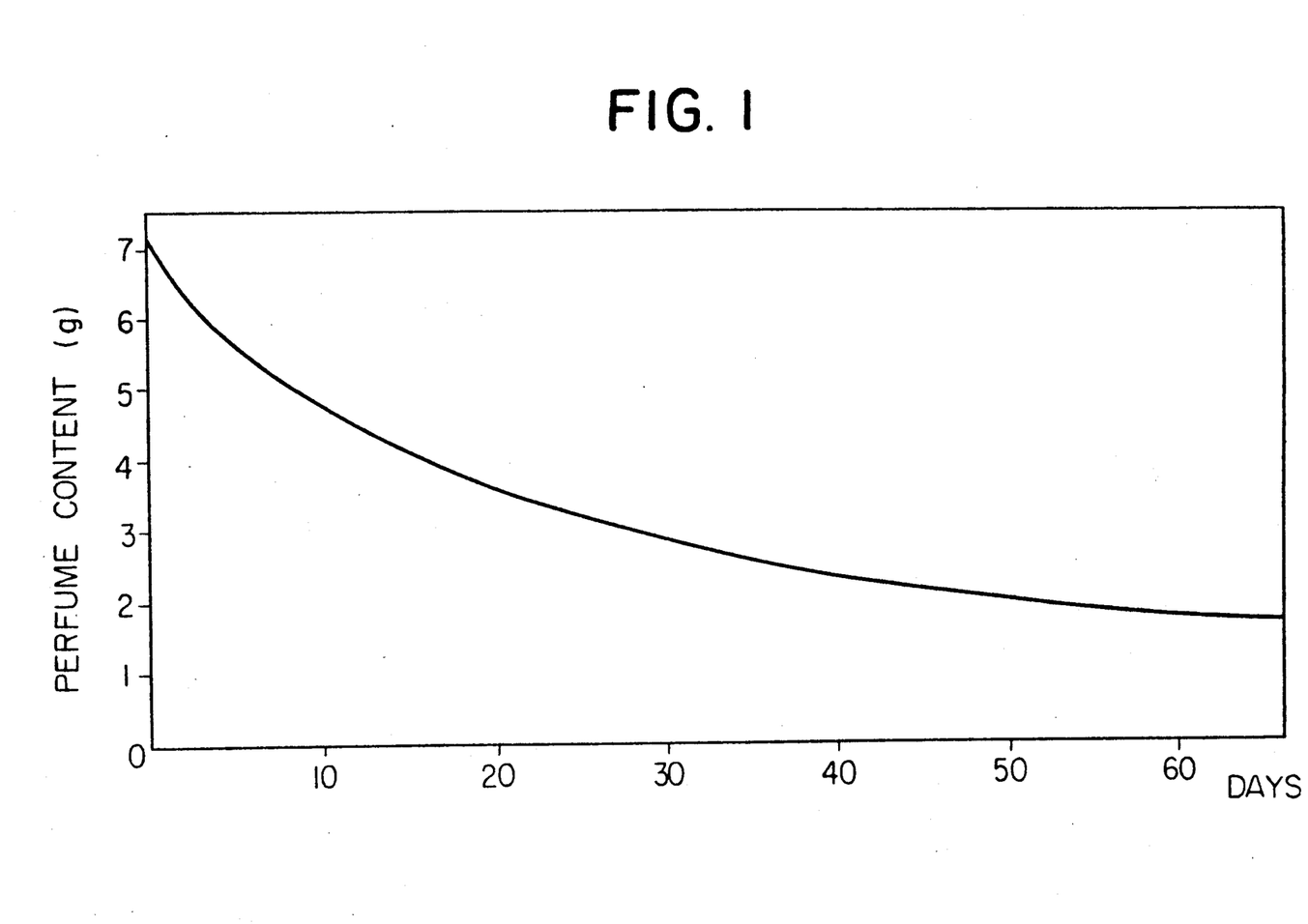
FIGS. 1 to 4 are diagrams showing volatilization curves with respect to the molded slow-release air fresheners obtained in the working examples, and showing the results of Examples 1, 2, 3 and 5, respectively, in which the perfume content (g) and the number of days are plotted along the axis of ordinate and the axis of abscissa, respectively.

This perfume-absorbed molded product was placed in a constant temperature chamber having a capacity of 4 m$^3$, held at 15° C. and a volatilization test was carried out over a period of 65 days, involving measuring the amount of the perfume volatilized at a predetermined certain time every day and conducting an organoleptic test. The results ware good as shown below.

| | |
|---|---|
| Total amount of perfume volatilized within the period | 5.341 g |
| Average amount of perfume volatilized a day | 82.17 mg |
| Percent volatilization (Volatilized amount/Perfume content × 100) | 76.3% |
| Strength of fragrance within the period (according to the six-stage odor indication method prescribed by the Environmental Agency) | 4 ~ 2.5 |
| Volatilizing property | as shown in FIG. 1 |

| Note 1: Strength | Six-Stage Odor Indication Method (Environmental Agency) State of Odor |
|---|---|
| 0 | Odorless |
| 1 | Slightly perceivable (threshold of perception) |
| 2 | Weak odor permitting recognition of the kind of odor (threshold of recognition) |
| 3 | Easily perceivable |
| 4 | Strong odor |
| 5 | Intense odor |

EXAMPLE 2

Figure 2:
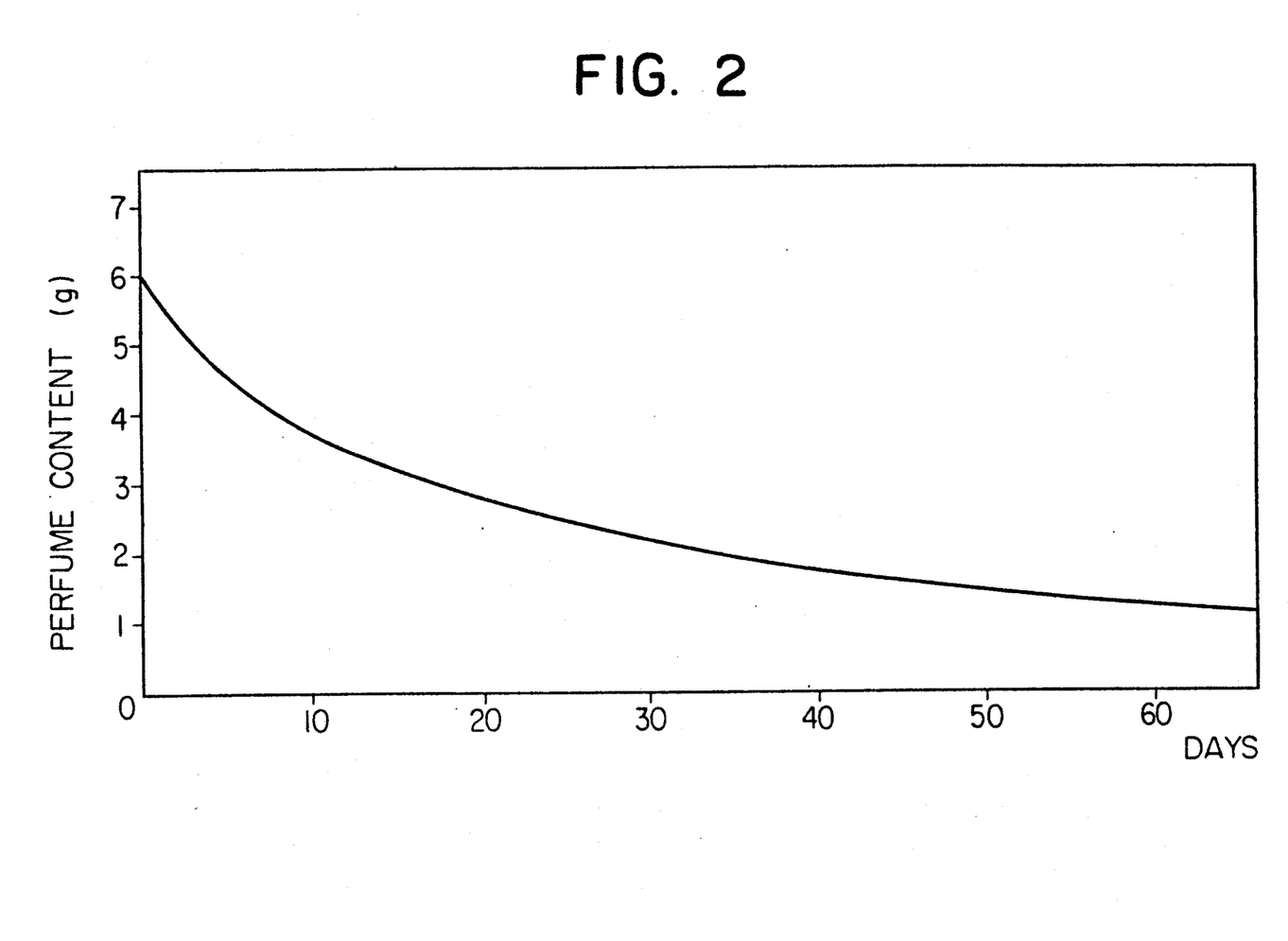

Powder not larger in particle size than 30 mesh of EVA, trade name "Ultrathene UE-710" (MI 18, VA content 28%, MP 75° C.), a product of Toyo Soda Manufacturing Co., Ltd., was charged (7.4 g) into a metallic can cap-like mold for melt bonding and molding 56 mm in diameter and 7 mm in depth, up to the brim of the mold, under application of pressure. Then, the mold was placed and heated in a constant temperature bath held at 77° C., and when the temperature of a temperature measuring, powder-charged, melt bonding mold like that used in Example 1 indicated 76° C. (MP+1° C.)(after 30 minutes), the can cap-like mold was taken out and cooled to room temperature. Then, the contents of the mold was removed from the mold to obtain a somewhat elastic, porous, melt-bonded, molded product having the appearance of a powder aggregate and having continuous gas-permeable pores, 4.4 mm in thickness. Its bulk density was 0.605 g/cm$^3$. This melt-bonded, molded product was placed in a tin can having a diameter of 70 mm and a depth of 10 mm and then 6 g (corresponding to 44.77% perfume content) of a lemony mixed perfume pre-colored into yellow with an oil-soluble dye was poured onto the central part of the surface of the melt-bonded, molded product. As a result, in an instant of 10 to 15 seconds the perfume was diffused and permeated over the whole surface of the molded product. Then, while expanding the molded product gradually, the perfume was absorbed into each of the powder particles as constituents of the molded product, and in five minutes there was obtained a strong, spongy, elastic product in a dried condition without wetting or stain with the perfume even under the application of a finger tip pressure, that is, in a state with no perfume remaining in the continuous gas-permeable pores of the melt-bonded, molded product. The expansion ratio was 1.53 times the original size in terms of surface area. This perfume-absorbed molded product was placed in a constant temperature chamber having a capacity of 4 m$^3$, held at 15° C. and a volatilization test was conducted over a period of 65 days, involving measuring the amount of the perfume volatilized at a predetermined certain time every day and conducting an organoleptic test. The results were good as shown below.

| | |
|---|---|
| Total amount of perfume volatilized within the period | 4.836 g |
| Percent volatilization (4.836/6 × 100) | 80.6% |
| Strength of fragrance | 4.25  2.5 |
| Volatilizing property | as shown in FIG. 2 |

EXAMPLE 3

Figure 3:
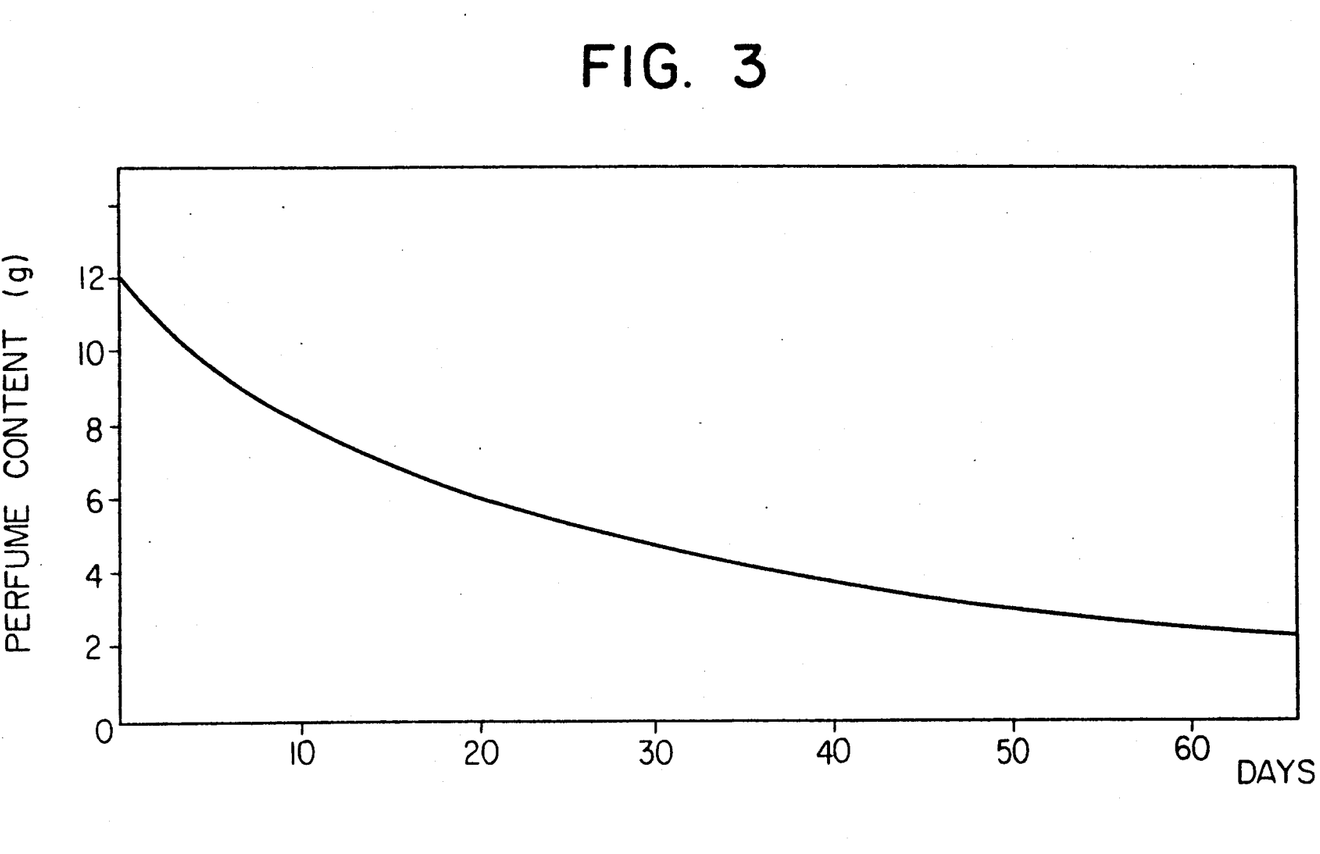

Powder not larger in particle size than 60 mesh (this size was adopted in order to increase the number of melt-bonded points of the powder particles to enhance the bonding force to an extent sufficient to resist hemispheric expansion) of EVA, trade name "Ultrathene UE-634" (MI 4, VA content 26%, MP 79° C.), a product of Toyo Soda Manufacturing Co., Ltd., was charged (12 g) into a metallic, can cap-like melt-bonding mold having a diameter of 75 mm and a depth of 6 mm, up to the brim of the mold. Then, the mold was placed and heated in a constant temperature bath held at 83° C., and when the temperature of a temperature measuring, powder-charged, melt-bonding mold like that used in Example 1 indicated 82° C. (after 30 minutes), the can cap-like mold was taken out and cooled to room temperature. Then, the contents of the mold was removed from the mold to obtain a somewhat elastic, porous, melt-bonded, molded product having the appearance of a powder aggregate and having continuous gas-permeable pores, 4.7 mm in thickness. Its bulk density was 0.578 g/cm$^3$. This disc-like, melt-bonded, molded product was fitted in a tin can having a diameter of 75 mm (same as the diameter of the melt-bonded, molded product) and a depth of 7 mm and having an upper edge somewhat rolled inside to fix the outer edge of the melt-bonded, molded product upon perfume absorption and expansion. Then, 12 g of a liquid mixture consisting of 6 g of a forest odor-like mixed perfume pre-colored into yellowish green with an oil-soluble dye and 6 g of an isoparaffinic odorless solvent "Shellsol-71" (BP 174°-207° C., a product of Shell Chemistry Co., Ltd.) was poured onto the central part of the surface of the melt-bonded, molded product. As a result, in 15 seconds the liquid mixture was diffused and permeated over the whole surface of the molded product. As it was absorbed into each of the powder particles, the molded product began to expand. Since the outer periphery of the molded product was held by the inwardly rolled upper edge of the can, the expansion was observed only upwards. After 8 minutes, there was obtained a strong, spongy, elastic product having a completely dry surface, that is, with no perfume remaining in the continuous gas-permeable pores, and having a height from the bottom to the top as large as 33 mm, in a hemispheric shape like a hollow ball cut in half. (The content of the solvent-diluted perfume was 50%.) This hemispheric perfume-absorbed molded product with the solvent-diluted perfume absorbed therein was placed in a constant temperature chamber having a capacity of 4 m³, held at 15° C. and a volatilization test was conducted over a period of 65 days, involving measuring the amount of the perfume volatilized at a predetermined certain time every day and conducting an organoleptic test. The results were good as shown below.

| | |
|---|---|
| Total amount of perfume volatilized within the period | 9.751 g |
| Average amount of perfume volatilized a day | 150.0 mg |
| Percent volatilization | 81.26% |
| Strength of fragrance within the period | 4.5 2.75 |
| Percent contraction (Surface area at the end of volatilization/Surface area at maximum expansion × 100) (Provided the shape at the end of volatilization was like a convex lens having a height of 12 mm up to the top.) | 67.6% |
| Volatilizing property | as shown in FIG. 3 |

EXAMPLE 4

Powders not larger in particle size than 30 mesh of EVA's, trade names "Ultrathene UE-720" (MI 150, VA content 28%, MP 74° C.), "Ultrathene UE-781" (MI 350, VA content 20%, MP 85° C.) and "Ultrathene UE-633" (MI 20, VA content 20%, MP 85° C.), products of Toyo Soda Manufacturing Co., Ltd., were each charged 6.5 g into a metallic, can cap-like melt-bonding mold having a diameter of 56 mm and a depth of 7 mm, up to the brim of the mold. Then, the molds thus charged with the powders were placed in constant temperature baths held at 70° C., 79° C. and 87° C. for Ultrathene UE-720, Ultrathene UE-681 and Ultrathene UE-633, respectively, and when the temperatures of such melt bonding temperature measuring molds with thermocouples embedded therein as mentioned in Examples 1 to 3 indicated 69° C. (MP −5° C.) in Ultrathene UE-720, 78° C. (MP −7° C.) in Ultrathene UE-681 and 86° C. (MP) in Ultrathene UE-633, (after approximately 25 to 35 minutes), the can cap-like molds were taken out and cooled to room temperature. Thereafter, the contents of the molds were removed from the molds to obtain somewhat elastic, porous, melt-bonded, molded products each having the appearance of a powder aggregate and having continuous gas-permeable pores, 5 mm or so in thickness.

The melt-bonded, molded products thus obtained were found to have bulk densities of 0.586 g/cm³ (Ultrathene UE-720), 0.627 g/cm³ (Ultrathene UE-681) g/cm³ and 0.609 g/cm³ (ultrathene UE-633). Those molded products were placed in tin cans each having a diameter of 70 mm and a depth of 10 mm and a fragrant olive type mixed perfume pre-colored into orange color was poured and absorbed into each of the molds in an amount affording a % perfume content corresponding to a value 1.6 times as large as the % VA content (Ultrathene UE-720, 28% × 1.6 = 44.8%, 6.5/0.552 − 6.5 = 5.2, the amount of perfume added, 5.2 g; Ultrathene UE-681 and Ultrathene UE-633, 20% × 1.6 = 32%, 6.5/0.68 − 6.5 = 3.06, the amount of perfume added, 3.06 g). As a result, the molded products expanded to 1.44 times (Ultrathene UE-720), 1.2 times (Ultrathene UE-681) and 1.23 times (Ultrathene UE-633), affording spongy elastic products.

The perfume-absorbed molded products thus obtained were subjected to a volatilization test in the same way as in Examples 1 to 3. As a result, all of them exhibited good violatilizing properties like the results obtained in those Examples.

EXAMPLE 5

Powder wholly passing through 32 mesh (average particle diameter: 0.5 mm) of EVA, trade name "Ultrathene UE-634", a product of Toyo Soda Manufacturing Co., Ltd., was charged into a metallic, can cap-like melt bonding mold having a diameter of 56 mm and a depth of 7 mm, and a melt-bonded, molded product having a weight of 6.4 g and a bulk density of 0.551 was obtained in the same manner and under the same conditions as in Example 3. Then, 6.4 g of a fragrant olive type mixed perfume was absorbed (perfume content: 50%) into the melt-bonded, molded product, allowing the latter to expand into a disc-like perfume-absorbed molded product having a diameter of 67 mm (1.43 times the original surface area), which will hereinafter be referred to as Sample-1.

Likewise, using 50 parts of Ultrathene UE-634 and 50 parts of a fragrant olive type mixed perfume, there was prepared an almost transparent, disc-like, perfume-containing melt-molded product (perfume content: 6.4 g) having a diameter of 68 mm, a thickness of 4 mm and a weight of 12.8 g, designated Sample-2.

Figure 4:
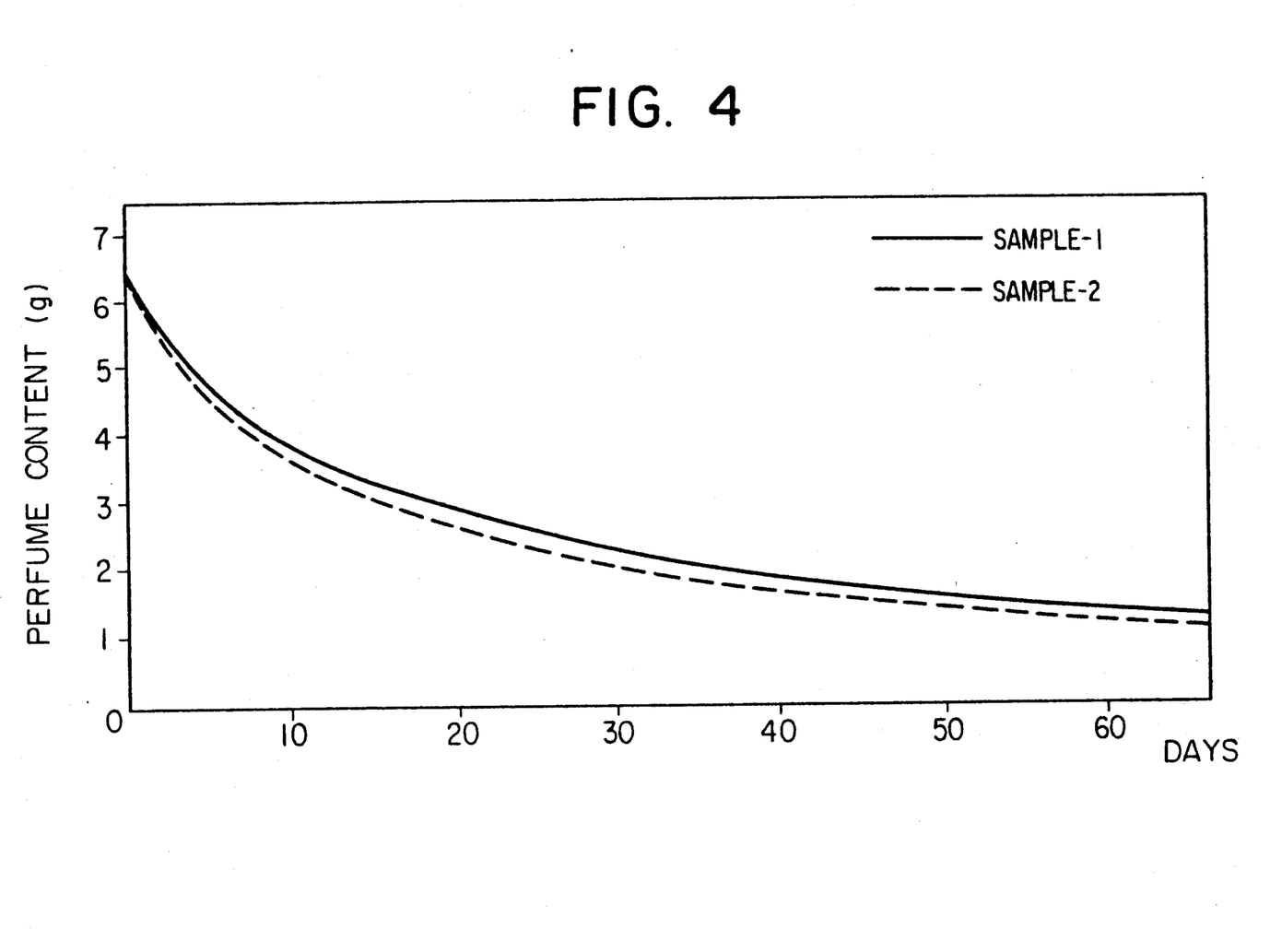

Sample-1 and Sample-2 were each charged into a flat-bottomed circular can having a diameter of 75 mm and a depth of 20 mm, then the cans were placed in a constant temperature chamber held at 15° C. and a volatilization test was conducted over a period of 65 days, involving measuring the amount of the perfume volatilized at a predetermined certain time. The results are as shown below. Both Sample-1 and Sample-2 exhibited about the same volatilizing properties.

| | Sample-1 | Sample-2 |
|---|---|---|
| Total amount of perfume volatilized within the period | 5.138 g | 5.297 g |
| Average amount of perfume volatilized a day | 79.05 mg | 81.49 mg |
| Percent volatilization | 80.28% | 82.77% |
| Volatilizing property | as shown in FIG. 4 | |

What is claimed is:

1. A molded slow-release air freshener prepared by having a liquid perfume composition absorbed into a porous sheet-like product which has been obtained by partially melt-bonding the particles of an ethylene-vinyl acetate copolymer powder in the form of a sheet with each other to obtain said porous sheet-like product having continuous gas-permeable pores and a bulk density in the range of 0.4 to 0.8 g/cm³, said molded slow-release air freshener having an increased apparent volume of at least 1.2 times as large as its apparent volume before the absorption of said liquid perfume composition.

2. A molded slow-release air freshener as set forth in claim 1, wherein said ethylene-vinyl acetate copolymer has a vinyl acetate content in the range of 6 to 40% by weight.

3. A molded slow-release air freshener as set forth in claim 1, wherein said ethylene-vinyl acetate copolymer powder has an average particle diameter not larger than 1 mm.

4. A molded slow-release air freshener as set forth in claim 2, wherein said liquid perfume composition comprises a perfume or both a perfume and a solvent and its content is not lower than a weight percent corresponding to the weight percent of the vinyl acetate content of said ethylene-vinyl acetate copolymer, and wherein the perfume composition does not remain in said continuous gas-permeable pores.

5. A molded slow-release air freshener as set forth in claim 1, which is in the form of a hollow hemisphere.

6. A molded slow-release air freshener comprising:
particles of ethylene-vinyl acetate copolymer which have been partially melt-bonded with each other to form a porous sheet-like product, said porous sheet-like product having continuous gas-permeable pores and a bulk density in the range of 0.4 to 0.8 g/cm$^3$;
a holder for said porous sheet-like product, said holder being in close-fitting relation to said porous sheet-like product and disposed about a portion of said porous sheet-like product;
a liquid perfume composition, said composition being absorbed into said porous sheet-like product and resulting in an expansion of said porous sheet-like product.

7. A molded slow-release air freshener as set forth in claim 6, wherein said porous sheet-like product has a plate-like shape prior to said expansion.

8. A molded slow-release air freshener as set forth in claim 6, wherein said expansion occurs in three dimensions.

9. A molded slow release air freshener as set forth in claim 6 wherein said expansion results in a hemispheric shape.

10. A molded slow-release air freshener as set forth in claim 6 wherein said ethylene vinyl acetate copolymer powder has a vinyl acetate content in the range of 6 to 40% by weight.

11. A molded slow-release air freshener as set forth in claim 6 wherein said ethylene vinyl acetate copolymer powder has an average particle diameter of no larger than 1 mm.

12. A molded slow-release air freshener as set forth in claim 6 wherein said liquid perfume composition comprises a perfume or a perfume and a solvent, and its weight percentage is not lower than the weight percentage of the vinyl acetate in said ethylene vinyl acetate copolymer and wherein said liquid perfume composition evaporates, after a period of time, from said continuous gas-permeable pores.

13. A molded slow-release air freshener comprising:
a porous molded product which has a been obtained by partially melt-bonding the particles of an ethylene-vinyl acetate copolymer powder with each other to obtain said porous molded product having continuous gas-permeable pores and a bulk density in the range of 0.4 to 0.8 g/cm$^3$;
a holder disposed about a portion of said porous molded product;
a liquid perfume composition absorbed into said porous molded product;
whereby said porous molded product can be increased to a size of at least 1.06 times greater than it size before the absorption of said liquid perfume composition, and can be three-dimensionally transfigured in appearance after the absorption of said liquid perfume composition.

14. A molded slow-release air freshener as set forth in claim 13 wherein the inside of said holder tapers off at an inward angle at least at those portions disposed about said porous molded product, thus permitting the porous molded product to shift toward the vertical direction during the transfiguration.

15. A molded slow-release air freshener as set forth in claim 13 wherein said holder is a container which engages the perimeter of said porous molded product.

16. A molded slow-release air freshener as set forth in claim 15 wherein said three-dimensional transfiguration in appearance after the absorption of said liquid perfume composition comprises a hollow space shaped between said porous molded product and said container.

17. A molded slow-release air freshener as set forth in claim 15 wherein said porous molded product is in the form of a circle-like sheet and said container has a circle-like surrounding wall and a diameter approximating that of said porous molded product, whereby after the absorption of said liquid perfume composition into said porous molded product a hollow hemisphere is formed at least around the center of said circle-like sheet.

18. A molded slow-release air freshener, as set forth in claim 17 wherein said porous molded product is in the form of an equilateral polygon-like sheet.

19. A molded slow-release air freshener as set forth in claim 13 wherein said ethylene vinyl acetate copolymer powder has a vinyl acetate content in the range of 6 to 40% by weight.

20. A molded slow-release air freshener as set forth in claim 13 wherein said ethylene vinyl acetate copolymer powder has an average particle diameter of no larger than 1 mm.

21. A molded slow-release air freshener as set forth in claim 13 wherein said liquid perfume composition comprises a perfume or a perfume and a solvent, and its weight percentage is not lower than the weight percentage of the vinyl acetate in said ethylene vinyl acetate copolymer and wherein said liquid perfume composition evaporates, after a period of time, from said continuous gas-permeable pores.

22. A molded slow-release air freshener comprising:
an absorbed porous molded product prepared by absorbing a liquid perfume composition into a porous molded product, said porous molded product having an obtained by partially melt-bonding particles of an ethylene vinyl acetate copolymer powder with each other to obtain said porous molded product having continuous gas-permeable pores and a bulk density in the range of 0.4 to 0.8 g/cm$^3$;
a holder disposed about a portion of said absorbed, porous molded product;
whereby said absorbed, porous molded product has a lengthened apparent size of at least 1.06 times as long as its apparent length before the absorption of said liquid perfume composition.

23. A molded slow-release air freshener as set forth in claim 22 wherein the inside of said holder tapers off at an inward angle at least at those portions disposed about said absorbed, porous molded product.

24. A molded slow-release air freshener as set forth in claim 22 wherein said holder is a container which engages the perimeter of said absorbed, porous molded product.

25. A molded slow-release air freshener as set forth in claim 24 wherein a hollow space is shaped between said absorbed porous molded product and said container such that the appearance of said absorbed, porous molded product is transfigured in three dimensions.

26. A molded slow-release air freshener as set forth in claim 24 wherein said absorbed, porous molded product has the form of a hollow hemisphere at least around the center of said absorbed, porous molded product.

27. A molded slow-release air freshener as set forth in claim 22 wherein said ethylene vinyl acetate copolymer powder has a vinyl acetate content in the range of 6 to 40% by weight.

28. A molded slow-release air freshener as set forth in claim 22 wherein said ethylene vinyl acetate copolymer powder has an average particle diameter of no larger than 1 mm.

29. A molded slow-release air freshener as set forth in claim 22 wherein said liquid perfume composition comprises a perfume or a perfume and a solvent, and its weight percentage is not lower than the weight percentage of the vinyl acetate in said ethylene vinyl acetate copolymer and wherein said liquid perfume composition evaporates, after a period of time, from said continuous gas-permeable pores.

30. A process for producing a molded slow-release air freshener, which comprises:
providing an ethylene-vinyl acetate copolymer powder in the form of a sheet;
heating said powder and thereby allowing the powder particles of said ethylene-vinyl acetate copolymer to be partially melt-bonded with each other to prepare a porous sheet having continuous gas-permeable pores and a bulk density in the range of 0.4 to 0.8 g/cm$^3$; and
impregnating, in a container, at least part of said porous sheet with a liquid perfume composition, said container disposed about said porous sheet wall.

31. A process as set forth in claim 30, wherein said heating is performed using a constant temperature bath at a temperature in the range of the melting point of the ethylene-vinyl acetate copolymer used minus 7° C. to said melting point plus 4° C.

32. A process as set forth in claim 30, wherein said container has a circular surface shape.

33. A process as set forth in claim 30, wherein said container has a surface area about the same as the surface area of said sheet.

34. A process as set forth in claim 30, wherein said heating takes place without the application of pressure.

35. A process for producing a molded slow-release air freshener which comprises:
placing ethylene vinyl acetate copolymer powder in the form of a sheet;
heating said powder thereby allowing the particles of said ethylene vinyl acetate copolymer powder to be partially melt-bonded with each other to obtain a porous sheet having continuous gas-permeable pores and a bulk density in the range of 0.4 to 0.8 g/cm$^3$;
cutting at least part of said porous sheet to a desired shape; and
impregnating, in a container, said porous sheet with a liquid perfume composition, said container having a surrounding wall and being of a size approximately that of said shaped porous sheet so as to be in close-fitting relationship with at least two portions of said shaped porous sheet.

36. A process as set forth in claim 35 wherein said heating is performed using a constant temperature bath at a temperature in a range of the melting point of said ethylene vinyl acetate copolymer from 7° C. below said melting point to 4° C. above said melting point.

37. A process as set forth in claim 35 wherein said container has a circular surface shape.

38. A process as set forth in claim 35 further comprising a support upon which the ethylene vinyl acetate copolymer powder is placed in the form of a sheet.

39. A process as set forth in claim 38 wherein the support is a plate.

40. A process as set forth in claim 38 wherein the support is a belt.

41. A process as set forth in claim 38 wherein the support is heated.

* * * * *